US009205395B2

(12) United States Patent
Yan (10) Patent No.: US 9,205,395 B2
(45) Date of Patent: Dec. 8, 2015

(54) ENCAPSULATION (75) Inventor: Nianxi Yan, Appleton, WI (US)

(73) Assignee: Encapsys, LLC, Appleton, WI (US)

( * ) Notice: Subject to any disclaimer, the term of this patent is extended or adjusted under 35 U.S.C. 154(b) by 370 days.

(21) Appl. No.: 12/904,755

(22) Filed: Oct. 14, 2010

(65) Prior Publication Data

US 2011/0092605 A1 Apr. 21, 2011

Related U.S. Application Data (60) Provisional application No. 61/251,822, filed on Oct. 15, 2009.

(51) Int. Cl.
| | |
|---|---|
| A61K 47/42 | (2006.01) |
| A61K 47/06 | (2006.01) |
| A23P 1/04 | (2006.01) |
| B01J 13/14 | (2006.01) |
| A23L 1/00 | (2006.01) |
| A23L 1/22 | (2006.01) |
| A61K 9/50 | (2006.01) |
| B01J 13/10 | (2006.01) |
| A23L 1/29 | (2006.01) |

(52) U.S. Cl.
CPC .............. *B01J 13/14* (2013.01); *A23L 1/0032* (2013.01); *A23L 1/22016* (2013.01); *A61K 9/5057* (2013.01); *B01J 13/10* (2013.01)

(58) Field of Classification Search
CPC .......... A61K 47/42; A61K 47/06; A23L 1/29; A23P 1/04
USPC ....................................................... 514/774
See application file for complete search history.

(56) References Cited

U.S. PATENT DOCUMENTS

| | | | |
|---|---|---|---|
| 3,080,293 A | 3/1963 | Koff | |
| 4,411,933 A | 10/1983 | Samejima et al. | |
| 4,462,982 A | 7/1984 | Samejima et al. | |
| 4,622,244 A | 11/1986 | Lapka et al. | |
| 4,663,286 A | 5/1987 | Tsang et al. | |
| 4,952,402 A | 8/1990 | Sparks et al. | |
| 5,188,837 A | 2/1993 | Domb | |
| 5,204,029 A | 4/1993 | Morgan et al. | |
| 5,246,603 A * | 9/1993 | Tsaur et al. | 510/519 |
| 5,418,010 A | 5/1995 | Janda et al. | |
| 5,498,439 A | 3/1996 | Bonner | |
| 5,690,990 A | 11/1997 | Bonner | |
| 5,795,570 A | 8/1998 | Weber et al. | |
| 6,048,562 A | 4/2000 | Mandralis et al. | |
| 6,365,385 B1 | 4/2002 | Opara | |
| 6,818,296 B1 | 11/2004 | Garces et al. | |
| 6,932,984 B1 | 8/2005 | Babtsov et al. | |
| 6,974,592 B2 | 12/2005 | Yan | |
| 7,435,715 B2 | 10/2008 | Broeckx et al. | |
| 7,491,687 B2 | 2/2009 | Popplewell et al. | |
| 2002/0034550 A1 | 3/2002 | Quong | |
| 2004/0062778 A1* | 4/2004 | Shefer et al. | 424/400 |
| 2006/0240094 A1 | 10/2006 | Asano et al. | |
| 2007/0141211 A1 | 6/2007 | Kolar, Jr. et al. | |
| 2008/0277812 A1 | 11/2008 | Guisinger et al. | |

FOREIGN PATENT DOCUMENTS

WO WO 2008017962 A2 * 2/2008

OTHER PUBLICATIONS

Neutraceuticals: Designer Foods III Garlic, Soy, and Licorice, Ed. Paul A. Lachance, Ph.D., FACN, 1997, Food & Nutrition Press, Inc., p. 344.*
International Search Report for European Application PCT/US2010/002747 dated Oct. 14, 2012.

* cited by examiner

*Primary Examiner* — Sarah Pihonak
*Assistant Examiner* — Jason A Deck
(74) *Attorney, Agent, or Firm* — Fitch, Even, Tabin & Flannery LLP (57) ABSTRACT

Disclosed are encapsulating methods and encapsulated products. A payload material may be encapsulated within a wall material. The carrier material and payload material form a combination that is at least substantially solid at room temperature but that is sufficiently fluid at milling temperature to permit milling and subsequent encapsulation. The payload material may be, for instance, a bitter tasting material. In some embodiments, the microcapsules will serve a taste masking function. In other embodiments, the microcapsules may be used where a slow release of the payload material is desired.

13 Claims, 3 Drawing Sheets

ENCAPSULATION

CROSS-REFERENCE TO RELATED PATENT APPLICATION

This application claims the benefit of U.S. Provisional Application No. 61/251,822, filed Oct. 15, 2009, which is incorporated in its entirety herein by reference.

TECHNICAL FIELD

The invention is in the field of encapsulation. Certain embodiments are in the field of encapsulating methods, and other embodiments are in the field of encapsulated products.

BACKGROUND

Microencapsulated products have long been known. Generally, a microencapsulated product includes a wall material that surrounds an encapsulated core material. Innumerable uses for microencapsulated products have been described in the art, and conventional uses include, for instance, encapsulation of color developer material in carbonless copy papers. Exemplarily teachings as to microcapsules and their method of production are found, for instance, in U.S. Pat. Nos. 4,197,346; 4,725,905; 4,299,411; 5,164,126; and other patents assigned to Appleton Papers Inc., the assignee of the present application.

Microencapsulation technology is sometimes used in connection with food and medicinal products. Specifically, it is sometimes desired to mask the bitter tastes of ingredients that are orally administered. This is particularly true in the medicinal fields, where the bitter taste of the active agent can contribute to patient non-compliance in taking medicines. In accordance with some conventional techniques, bitter medicinal ingredients are microencapsulated within a capsule wall. The capsule wall is intended to block the diffusion of the material out of the microcapsules.

In this conventional approach, the microcapsule walls may lose their barrier properties when placed into contact with moisture, such as that present in the oral cavity. This is especially true when the wall is composed of gelatin, a common microcapsule wall material. If the capsule core is composed of a small molecule with a low viscosity, diffusion out of the capsule core and into the wall may occur, with equilibrium becoming established between the capsule core and the matrix. For some encapsulated payload ingredients, the taste threshold can be as low as parts-per-million, or even parts-per-billion in some cases. This threshold is detectable in the wall material, thereby making it difficult to mask taste effectively. This is especially true from small molecular bioactives in a liquid state that are intended for oral administration.

SUMMARY

Generally, a payload material, which may be, for instance, a bitter medicament, and a carrier material are disposed within a wall material. The payload material and carrier material together form a combination. In some embodiments, this combination is at least substantially hard at room temperature (roughly 25° C.) but at the higher temperatures of milling, the combination is sufficiently fluid to permit milling at the desired temperature. The carrier material may be any suitable material. In some embodiments, the carrier material is candelilla wax or paraffin wax.

In some embodiments, the invention provides a plurality of microcapsules, each comprising a payload material and carrier material disposed within a wall material, wherein the microcapsules include a ratio of the payload material to carrier material effective for providing microcapsules exhibiting a 168-hour hexane extraction concentration of not more than 85% of the carrier-free hexane extraction concentration. The hexane extraction concentration is as described hereinbelow, and the carrier-free hexane extraction concentration is the hexane extraction concentration of otherwise similar microcapsules prepared in the absence of the carrier material.

Also provided in some embodiments is a method for encapsulation. The method includes providing a combination of a payload material and carrier material, dispersing the combination into a wall material, milling to a desired droplet size, and precipitating wall material onto the droplets to form a plurality of microcapsules.

DETAILED DESCRIPTION

Generally, microcapsules may include a payload material in combination with a carrier material, and surrounded by a wall material. The payload material may be any material desired to be delivered via the microencapsulated product provided herein, and may be, for instance, any bioactive, pharmaceutical, nutraceutical or other compound or composition that is susceptible of microencapsulation. Exemplary bioactive materials include biocides, bactericides, insecticides, pesticides, fungicides, and the like. Generally, the payload material may be a water soluble material, an oil soluble material, a water-dispersible material, or an oil-dispersible material. Preferably the payload material is an oil or is an oil-soluble or oil-dispersible bioactive, pharmaceutical, or nutraceutical. The bioactive, pharmaceutical, or nutraceutical may be carried in a carrier oil. In some embodiments, the payload material may be a volatile oil, flavor oil, or essential oil.

In some embodiments, the payload material is not necessarily limited to one in which a taste-masking application is desired, and the material may be any material for which a delayed release into an environment is desired. For instance, the microcapsules in some embodiments are useful in connection with the introduction of a fertilizer compound into soil. In some embodiments, combinations of payload materials may be employed. In other embodiments the payload material is an oil such as a fragrance, a flavored oil or a material subject to degradation whose stability may be enhanced by microencapsulation. For example, the payload may be selected to be a material known to be light sensitive, such as certain vitamins, or oxygen sensitive, such as omega-3 oils. It is believed that stability of such materials will be enhanced in some embodiments of the invention.

The carrier material may be any material that is capable of forming a combination with the payload material wherein the carrier material and payload combination is at least substantially solid at room temperature but sufficiently flowable at milling temperature or higher temperature to permit milling and subsequent encapsulation within a desired wall material. The temperature of milling is typically in the range of 35-90° C., more typically 40-75° C., and in some embodiments 40-60° C., and in yet further embodiments, 50-60° C. The room temperature may be taken to be anywhere from 22 to 25° C. At 75° C. the carrier material may have a viscosity range of 1200 centipoise or less, 800 centipoise or less, from about 100 to 1200 centipoise, from about 100 to 800 centipoise, or even from about 800-1200 centipoise. Viscosities can be measured with a Brookfield viscometer (Model DV-II+) using spindle no. 6. In some embodiments, not mutually exclusive but not necessarily coextensive with the foregoing embodiments, the molecular weight of the carrier materials may be less than 3000 g/mol, in some embodiment less than 1000 g/mol, and in some embodiments less than 800 g/mol. The carrier material may be, for instance, a suitable candelilla or paraffin wax.

Alternatively, the carrier material may include materials such as esters, fatty acid derivatives, steroid derivatives, lecithin, or sorbitan monosterate. Fatty acid derivatives may include stearates, hydrogenated palm oil, and hydrogenataed vegetable oil. Steroid derivatives may include deoxycholic, cholic, apocholic, and lithocholic acids and their salts. Other carrier materials may include amino acid and organometallic compounds. The above materials may be used alone or in combinations with one another, or in combination with candellila wax and/or paraffin wax.

Figure 1:
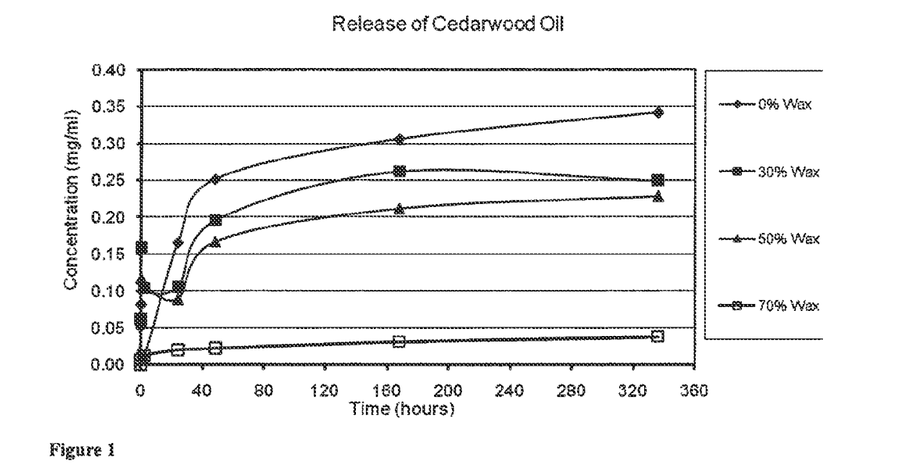
FIGS. 1 to 3 are graphs depicting hexane-extracted concentrations of three microencapsulated flavor oils with various levels of candelilla wax carrier material.
Figure 2:
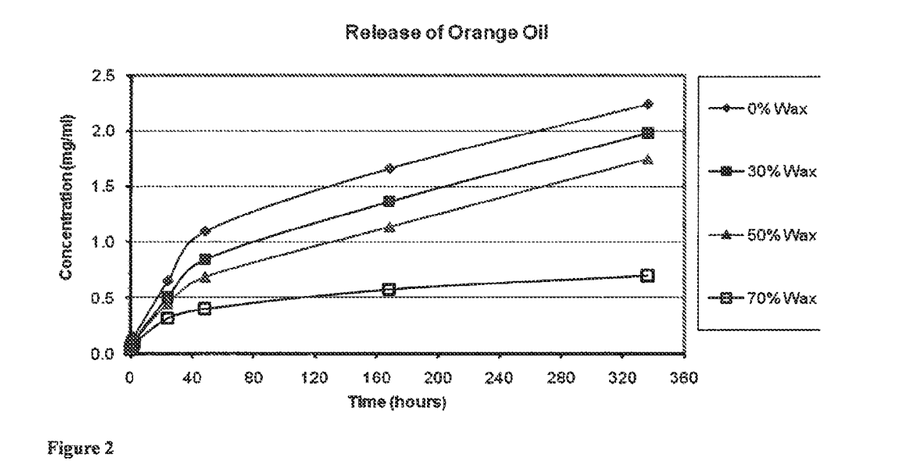
Figure 3:
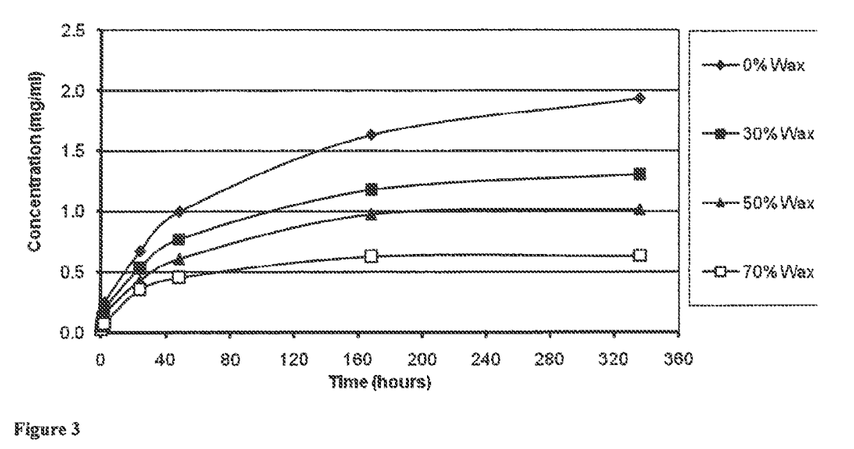
Figure 4:
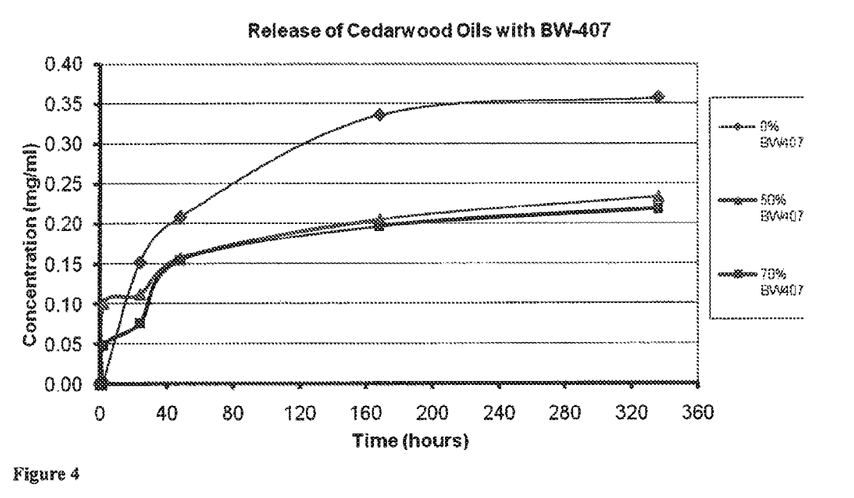
FIGS. 4 to 6 are graphs depicting hexane-extracted concentrations of three microencapsulated flavor oils with various levels of paraffin wax carrier material.
Figure 5:
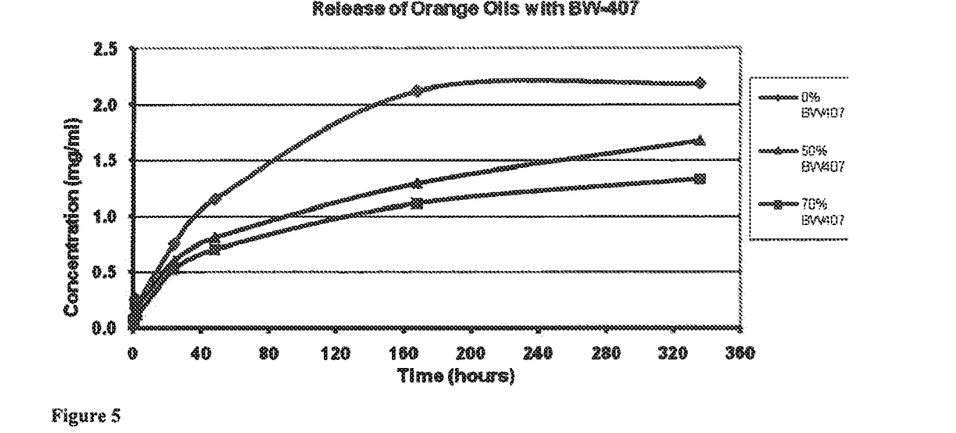
Figure 6:
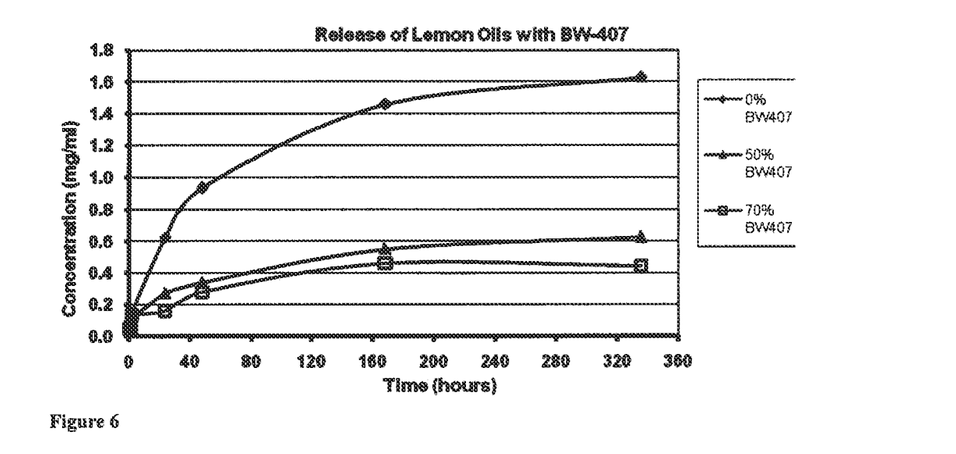

Any suitable ratio of carrier material to payload material may be employed in the combination. The ratio may have, for instance, 10% or greater payload material, 20% or greater payload material, 30% or greater payload material, 40% or greater payload material, 50% or greater payload material, 60% or greater payload material, 70% or greater payload material, 80% or greater payload material, or 90% or greater payload material. The balance may be carrier material, or other materials may be employed. In some embodiments, the selection of a ratio of payload material to carrier material may be employed in a given microencapsulation application. As is evident in the data in FIGS. 1-6, described in more detail hereinbelow, by adjusting the ratio of payload material to carrier material in the microcapsule core, different release properties may be thereby obtained. In some embodiments, such as those described below in certain of the examples, a carrier material and payload material may be suitable when employed together in some ratios but not others. In some embodiments of the invention, a selection is made of an appropriate ratio of carrier to payload material.

The wall material may be any suitable material. The wall material may be, for instance, gelatin or any other enteric or non-enteric material. The microcapsules can be prepared by processes well known in the art such as from gelatin as disclosed in U.S. Pat. Nos. 2,800,457 and 3,041,289; or, in some embodiments, from urea-formaldehyde resin and/or melamine-formaldehyde resin as disclosed in U.S. Pat. Nos. 4,001,140; 4,081,376; 4,089,802, 4,100,103; 4,105,823; 4,444,699 or 4,552,811. Alkyl acrylate-acrylic acid copolymer capsules, as taught in U.S. Pat. No. 4,552,811, may be employed. In some embodiments, the wall material may be polyurethane, polyurea, polyacrylate or polymethacrylate. Enteric materials can be used as the wall material and can include without limitation wall materials such as gelatin, cellulose acetate esters, hydroxypropyl methylcellulose esters, polymethacrylate copolymers, such as polymethacrylic acid-co-ethyl acrylate, polymethacrylic acid-co-methyl methacrylate, polyvinyl phthalate, polyvinyl acetate phthalate, shellac, and blends of the foregoing.

Common microencapsulation processes can be viewed as a series of steps. First, the core material which is to be encapsulated is emulsified or dispersed in a suitable dispersion medium. This medium is preferably aqueous but involves the formation of a polymer-rich phase. Frequently, this medium is a solution of the intended capsule wall material. The solvent characteristics of the medium are changed such as to cause phase separation of the wall material. The wall material is thereby contained in the liquid phase, which is also dispersed in the same medium as the intended capsule core material. The liquid wall material phase deposits itself as a continuous coating about the dispersed droplets of the internal phase or capsule core material. The wall is then solidified. The process is commonly known as coacervation.

Gelatin or gelatin-containing microcapsule wall material is well known. Phase separation processes, or coacervation processes are described in U.S. Pat. Nos. 2,800,457 and 2,800,458. Encapsulations based on polymerization of urea and formaldehyde, monomeric or low molecular weight polymers of dimethylol urea or methylated dimethylol urea, melamine and formaldehyde, methylated melamine formaldehyde, monomeric or low molecular weight polymers of methylol melamine or methylated methylol melamine, as taught in U.S. Pat. No. 4,552,811, may be employed. These materials are typically dispersed in an aqueous vehicle and the reaction is conducted in the presence of acrylic acid-alkyl acrylate copolymers.

Generally, a method for encapsulation as provided herein may include conventional steps, and may include providing a combination of a payload material and a carrier material as heretofore described, dispensing the combination into a wall material, milling to a desired droplet sized form of plurality of droplets, and causing precipitation of the wall material onto the droplets to thereby form a plurality of microcapsules. Any suitable processing conditions may be employed. The microcapsules thus formed may have any suitable size. Measured as an average size, the size may range, for instance, from 1 micron to 500 microns, preferably 1 micron to 100 microns, in some embodiments 1 micron to 50 microns and in other embodiments under 10-40 microns.

In one embodiment, the carrier material is mixed with the payload material at a milling temperature and introduced to an 8% gelatin solution at a pH of 7-8. High shear agitation is provided to the aqueous mixture to achieve a droplet size of less than about 250 microns, preferably less than 100 microns, and more preferably less than 50 microns. In certain applications smaller droplet sizes may be preferable. The mixture is stirred at a first temperature to effect capsule wall formation. It should be readily understood by those skilled in the art that this may be accompanied by a pH shift with wall materials such as gelatin to promote the phase separation in the wall formation step, as taught in patents such as U.S. Pat. Nos. 2,800,457 and 2,800,458. For instance, the pH may be lowered to around 4-6.

In many embodiments, a cross-linking agent will be added. Any suitable chemical or other cross-linking material conventionally known or otherwise found to be suitable for use for cross-linking a microcapsule shell material may be employed. For a food-grade application, an enzymatic cross linking agent, such as transglutanimase, may be employed. In other embodiments, other cross-linking agents may be employed, including aldehydes such as glutaraldehyde, genipin, tannic acid, alum, or a mixture thereof.

The resulting product will be a slurry of microcapsules, possibly including clusters of microcapsules. This product is deemed commercially useful itself. In many embodiments, it is desirable to dry these microcapsules to form substantially dry microcapsules. The microcapsules may be dried to any suitable moisture content, and in some cases are dried to yield a flowable powder. Any suitable drying method, such as spray-drying, may be employed.

In some embodiments, the payload material will be fixed within the microcapsules and will not be susceptible to rapid release. This makes the microcapsules suitable for taste-masking applications. In some embodiments, the microcapsules have a hexane extraction value, as described in the following examples, of less than 2 mg/ml at 168 hours. In other embodiments, the hexane extraction value is less than 1 mg/ml at 168 hours, and in other embodiments, it is less than 0.5 mg/ml at 168 hours. These values depend upon the material employed and on the ratio of payload material to carrier material. In some embodiments, the microcapsules have a 168-hour hexane extraction concentration of not more than 85% of the carrier-free hexane extraction concentration. This value may be not more than 80%; not more than 75%; not more than 70%; not more than 65%; not more than 60%; not more than 55%%; not more than 50%; not more than 45%; not more than 40%; or not more than 35% of the carrier-free hexane extraction concentration. These may be at any suitable ratio of payload material to carrier material.

In some embodiments, the microcapsules may be coated with an outer layer. For instance, an anti-swelling fatty material may be employed as a coating, such as animal and vegetable oils and fats, natural vegetable and animal waxes, non natural waxes, shellacs and gum lacs. Typical fats and waxes include partially hydrogenated vegetable oils, hydrogenated cotton seed oils, hydrogenated palm oils, hydrogenated castor oils, paraffin wax, candelilla wax, carnauba wax, Hoechst wax, beeswax, shellac, etc. Such coating is believed in some embodiments to enhance the taste-masking properties of the microcapsules. When used, the coating may be applied via any suitable technique. Conventional techniques include fluidized bed application, spraying, and double emulsion techniques.

The microcapsules may be used in any suitable application. In some embodiments, where a slow-release or taste-masking property is desired, microcapsules are deemed to be particularly suitable. In a taste-masked application, or other food or beverage application, a comestible product may be prepared using microcapsules as described herein in combination with another flavoring agent. Examples include beverages and medicines, such as children's oral medicines.

EXAMPLES

The following examples are provided. These examples are not intended to limit the scope of the invention. Examples with the prefix "C" are deemed comparative examples.

Example 1A, 1B and 1C

Cedarwood Oil with Carrier Candelilla Wax

Example 1A 30% Candelilla Wax 3 grams of candelilla wax (from Sigma-Aldrich) was dispersed into 7 grams of cedarwood oil (from Sigma-Aldrich, Saint Louis, Mo., U.S.A.) in a 20 ml vial to make up a 10 grams of a combination of candelilla wax and cedarwood oil.

Example 1B 50% Candelilla Wax 5 grams of candelilla wax (from Sigma-Aldrich) was dispersed into 5 grams of cedarwood oil (from Sigma-Aldrich, Saint Louis, Mo., U.S.A.) in a 20 ml vial to make up a 10 grams of a combination of candelilla wax and cedarwood oil.

Example 1C 70% Candelilla Wax 7 grams of candelilla wax (from Sigma-Aldrich, Saint Louis, Mo., U.S.A.) was dispersed into 3 grams of cedarwood oil (from Sigma-Aldrich, Saint Louis, Mo., U.S.A.) in a 20 ml vial to make up a 10 grams of a combination of candelilla wax and cedarwood oil.

The vials of Samples 1A, 1B and 1C were placed in a water bath (Cole-Parmer), and candelilla wax was slowly dissolved into cedarwood oil by raising temperature of the water bath. At 70° C., candelilla wax was completely dissolved, resulting in a clear, low viscosity solution.

The vials with Samples 1A, 1B and 1C were allowed to cool to room temperature at around 22° C. The properties of the contents in the vials were evaluated and are recorded in Table 1.

Example 1AC, 1D and 1E

Cedarwood Oil with BW-407 Paraffin Wax

Example 1AC 30% BW-407

3 grams of BW-407 (a paraffin wax from Blended wax, Inc., Oshkosh, Wis.) was dispersed into 7 grams of cedarwood oil (from Sigma-Aldrich, Saint Louis, Mo., U.S.A.) in a 20 ml vial to make up a 10 grams of a combination of BW-407 wax and cedarwood oil.

Example 1D 50% BW-407

5 grams of BW-407 (a paraffin wax from Blended wax, Inc., Oshkosh, Wis.) was dispersed into 5 grams of cedarwood oil (from Sigma-Aldrich, Saint Louis, Mo., U.S.A.) in a 20 ml vial to make up a 10 grams of a combination of BW-407 and cedarwood oil.

Example 1E 70% BW-407

7 grams of BW-407 (a paraffin wax from Blended wax, Inc., Oshkosh, Wis.) was dispersed into 3 grams of cedarwood oil (from Sigma-Aldrich, Saint Louis, Mo., U.S.A.) in a 20 ml vial to make up a 10 grams of a combination of BW-407 and cedarwood oil.

The vials of Examples 1 AC, 1D, and 1E were placed in a water bath (Cole-Parmer), and BW-407 was slowly dissolved into cedarwood oil by raising temperature of the water bath. At 60° C., BW-407 was completely dissolved, resulting in a clear, low viscosity solution. The vials were allowed to cool to room temperature at around 22° C. The properties of the contents in the vials were evaluated and are recorded in Table 1.

Example 2A, 2B and 2C

Orange Oil with Carrier Candelilla Wax

Example 2A 30% Candelilla Wax 3 grams of candelilla wax (from Sigma-Aldrich, Saint Louis, Mo., U.S.A.) was dispersed into 7 grams of orange oil (from Sigma-Aldrich, Saint Louis, Mo., U.S.A.) in a 20 ml vial to make up a 10 grams of a combination of candelilla wax and orange oil.

Example 2B 50% Candelilla Wax 5 grams of candelilla wax (from Sigma-Aldrich, Saint Louis, Mo., U.S.A.) was dispersed into 5 grams of orange oil (from Sigma-Aldrich, Saint Louis, Mo., U.S.A.) in a 20 ml vial to make up a 10 grams of a combination of candelilla wax and orange oil.

Example 2C 70% Candelilla Wax 7 grams of candelilla wax (from Sigma-Aldrich, Saint Louis, Mo., U.S.A.) was dispersed into 3 grams of orange oil (from Sigma-Aldrich, Saint Louis, Mo., U.S.A.) in a 20 ml vial to make up a 10 grams of a combination of candelilla wax and orange oil.

The vials of Examples 2A, 2B and 2C were placed in a water bath (Cole-Parmer), and candelilla wax was slowly dissolved into orange oil by raising temperature of the water bath. At 75° C., candelilla wax was completely dissolved, resulting in a clear, low viscosity solution. The vials were allowed to cool to room temperature at around 22° C. The properties of the contents in the vials were evaluated and are recorded in Table 1.

Example D, E and F

Orange Oil with BW-407 Paraffin Wax

Example D 30% BW-407

3 grams of BW-407 (a paraffin wax from Blended wax, Inc., Oshkosh, Wis.) was dispersed into 7 grams of orange oil (from Sigma-Aldrich, Saint Louis, Mo., U.S.A.) in a 20 ml vial to make up 10 grams of a combination of BW-407 and orange oil. The BW-407 wax is characterized as a white, hard, low melt point, paraffin wax having a congealing point in the range from 127-132° F./53-56° C.

Example E 50% BW-407

5 grams of BW-407 was dispersed into 5 grams of orange oil (from Sigma-Aldrich, Saint Louis, Mo., U.S.A.) in a 20 ml vial to make up 10 grams of a combination of BW-407 and orange oil.

Example F 70% BW-407

7 grams of BW-407 was dispersed into 3 grams of orange oil (from Sigma-Aldrich, Saint Louis, Mo., U.S.A.) in a 20 ml vial to make up 10 grams of a combination of BW-407 wax and orange oil.

The vials of Samples D, E and F were placed in a water bath (Cole-Parmer), and BW-407 wax was slowly dissolved into orange oil by raising temperature of the water bath. At 60° C., BW-407 wax was completely dissolved, resulting in a clear, low viscosity solution. The vials were allowed to cool to room temperature at around 22° C. The properties of the contents in the vials were evaluated and are recorded in Table 1.

Example 3A, 3B and 3C

Lemon Oil with Carrier Candelilla Wax

Example 3A 30% Candelilla Wax 3 grams of candelilla wax (from Sigma-Aldrich, Saint Louis, Mo., U.S.A.) was dispersed into 7 grams of lemon oil (from Sigma-Aldrich, Saint Louis, Mo., U.S.A.) in a 20 ml vial to make up a 10 grams of a combination of candelilla wax and lemon oil.

Example 3B 50% Candelilla Wax 5 grams of candelilla wax (from Sigma-Aldrich, Saint Louis, Mo., U.S.A.) was dispersed into 5 grams of lemon oil (from Sigma-Aldrich, Saint Louis, Mo., U.S.A.) in a 20 ml vial to make up a 10 grams of a combination of candelilla wax and lemon oil.

Example 3C 70% Candelilla Wax 7 grams of candelilla wax (from Sigma-Aldrich, Saint Louis, Mo., U.S.A.) was dispersed into 3 grams of lemon oil (from Sigma-Aldrich, Saint Louis, Mo., U.S.A.) in a 20 ml vial to make up a 10 grams of a combination of candelilla wax and lemon oil.

The vials of Samples 3A, 3B and 3C were placed in a water bath (Cole-Parmer), and candelilla wax was slowly dissolved into lemon oil by raising temperature of the water bath. At 75° C., candelilla wax was completely dissolved, resulting in a clear, low viscosity solution. The vials were allowed to cool to room temperature at around 22° C. The properties of the contents in the vials were evaluated and are recorded in Table 1.

Example 3AC, G and 3D

Lemon Oil with BW-407 Paraffin Wax

Example 3AC 30% BW-407

3 grams of BW-407 was dispersed into 7 grams of lemon oil (from Sigma-Aldrich, Saint Louis, Mo., U.S.A.) in a 20 ml vial to make up a 10 grams of a combination of BW-407 wax and lemon oil.

Example G 50% BW-407

5 grams of BW-407 was dispersed into 5 grams of lemon oil (from Sigma-Aldrich, Saint Louis, Mo., U.S.A.) in a 20 ml vial to make up a 10 grams of a combination of BW-407 and lemon oil.

Example 3D 70% BW-407

7 grams of BW-407 was dispersed into 3 grams of lemon oil (from Sigma-Aldrich, Saint Louis, Mo., U.S.A.) in a 20 ml vial to make up a 10 grams of a combination of BW-407 and lemon oil.

The vials of Samples 3AC, G and 3D were placed in a water bath (Cole-Parmer), and BW-407 was slowly dissolved into lemon oil by raising temperature of the water bath. At 60° C., BW-407 was completely dissolved, resulting in a clear, low viscosity solution. The vials were allowed to cool to room temperature at around 22° C. The properties of the contents in the vials were evaluated and are recorded in Table 1.

Example 4AC, 4A, and 4B

Peppermint Oil with Carrier Candelilla Wax

Example 4AC 30% Candelilla Wax 3 grams of candelilla wax (from S Sigma-Aldrich, Saint Louis, Mo., U.S.A.) was dispersed into 7 grams of peppermint oil (from Sigma-Aldrich, Saint Louis, Mo., U.S.A.) in a 20 ml vial to make up a 10 grams of a combination of candelilla wax and peppermint oil.

Example 4A 50% Candelilla Wax 5 grams of candelilla wax (from Sigma-Aldrich, Saint Louis, Mo., U.S.A.) was dispersed into 5 grams of peppermint oil (from Sigma-Aldrich, Saint Louis, Mo., U.S.A.) in a 20 ml vial to make up a 10 grams of a combination of candelilla wax and peppermint oil.

Example 4B 70% Candelilla Wax 7 grams of candelilla wax (from Sigma-Aldrich, Saint Louis, Mo., U.S.A.) was dispersed into 3 grams of peppermint oil (from Sigma-Aldrich, Saint Louis, Mo., U.S.A.) in a 20 ml vial to make up a 10 grams of a combination of candelilla wax and peppermint oil.

The vials of Samples 4AC, 4A, and 4B were placed in a water bath (Cole-Parmer), and candelilla wax was slowly dissolved into peppermint oil by raising temperature of the water bath. At 75° C., candelilla wax was completely dissolved, resulting in a clear, low viscosity solution. The vials were allowed to cool to room temperature at around 22° C. The properties of the contents in the vials were evaluated and are recorded in Table 1.

Several samples of microcapsules were prepared. The samples were made by blending the carrier material and the oil at a temperature of 60 to 75° C. to form a combination. A solution of 8% gelatin was prepared and the combination was dispersed into the gelatin solution. The microcapsules were milled to a size of 5 microns in a jacketed stainless reactor, and upon cooling, the gelatin material was precipitated onto the droplet surface to form a capsule wall. The following table indicates the products that were prepared, including the payload material, the carrier material, and the percentage of carrier in the payload/carrier combination.

TABLE 1

Combination of Carrier Materials and Flavor Oils

| Example | Oil | Gelling Agents | Temperature | Carrier Percentage In Combination 30% | 50% | 70% |
|---|---|---|---|---|---|---|
| 1A, 1B, 1C | Cedarwood oil | Candelilla Wax | 22 | hard | hard | very hard |
|  |  |  | 70 | Clear fluid | clear fluid | clear |
| 1AC, 1D, 1E |  | BW407 | 22 | soft | hard/brittle | hard |
|  |  |  | 60 | clear/brown | clear | clear |
| 2A, 2B, 2C | Orange Oil | Candelilla Wax | 22 | no flow | hard | very hard |
|  |  |  | 75 | clear | clear | clear |
| D, E, F |  | BW407 | 22 | Suspension | soft | punchable |
|  |  |  | 60 | clear | clear | clear |
| 3A, 3B, 3C | Lemon Oil | Candelilla Wax | 22 | no flow | hard | very hard |
|  |  |  | 75 | clear | clear | clear |
| 3AC, G, 3D |  | BW407 | 22 | Suspension | soft | punchable |
|  |  |  | 60 | clear | clear | clear |
| 4AC, 4A, 4B | Peppermint | Candelilla Wax | 20 | soft | hard | really hard |
|  |  |  | 75 | clear | clear | hazy/fines |

The flow properties of the carrier materials/oil combination at the listed temperatures also are indicated in the foregoing table. As seen, at 22° C. using candelilla wax, the combination was hard or non-flowing (except for peppermint oil/30% candelilla wax). At higher temperatures, the combination was sufficiently fluidic to permit milling. Certain of the experiments with BW-407 paraffin produced satisfactory microcapsules.

Combinations such as Example E or Example G were not as hard or non-flowable as other samples at room temperature, but they were effective for providing delay and slow release as compared to a flavor oil by itself. Hardness is not the only selection criterion in certain embodiments. Gel structure and interactions between flavor oils and carrier can also contribute to delay and slow release. While not intending to be bound by any theory, in certain embodiments, depending on the end use application, delay and slow release by the carrier material may be a function of specific oil and carrier combinations.

Examples 5-7

In separate runs, microcapsules were prepared according to the procedure heretofore described, the microcapsules containing in the core an essential oil or a flavor oil, and candelilla wax. The microcapsules contain a flavor oil selected from cedarwood oil, orange oil, or lemon oil. For each oil, four sets of microcapsules were prepared; the microcapsules containing 0% candelilla wax, 30% candelilla wax, 50% candelilla wax and 70% candelilla wax, respectively. These examples are enumerated in Table 2.

Example C5

Preparation of Microcapsules Containing Cedarwood Oil

In this example, a carrier was not employed in the microcapsule core. First, 31.8 grams of gelatin (Sigma-Aldrich, Saint Louis, Mo., U.S.A.) was mixed with 423 grams of deionized water in a jacketed reactor at 40° C. until completely dissolved. A sodium polyphosphate solution was prepared by dissolving 3.2 grams of sodium polyphosphate in 61 grams of deionized water. Subsequently, 15 grams of cedarwood oil (from Sigma-Aldrich, Saint Louis, Mo., U.S.A.) was emulsified into the gelatin solution with a four-blade mixer. An oil-in-water emulsion was formed with a median size of 8 µm analyzed with AccuSizer™ 780, (Particle Sizing Systems, Santa Barbara, Calif., U.S.A.). After 312 grams of deionized water was added to the reactor, the previously prepared sodium polyphosphate solution was added into the reactor. The pH was adjusted to 4.8 with 10% phosphoric acid solution. During pH adjustment and the cooling steps following the pH adjustment, a coacervate, formed from gelatin and polyphosphate, coated onto the oil droplets to form microcapsules. The capsule shells were cross linked with 8 grams of Activa TI (Ajinomoto U.S.A.) containing transglutaminase. The microcapsules suspended in water were then spray dried to obtain a free-flowing powder

Example 5A

Preparation of Microcapsules Containing 30% Candelilla Wax and 70% Cedarwood Oil 31.8 grams of gelatin (Sigma-Aldrich, Saint Louis, Mo., U.S.A.) was mixed with 423 grams of deionized water in a jacketed reactor at 70° C. until completely dissolved. A sodium polyphosphate solution was prepared by dissolving 3.2 grams of sodium polyphosphate in 61 grams of deionized water. A combination of candelilla wax and cedarwood oil was obtained by mixing 4.5 grams of candelilla wax with 10.5 grams of cedarwood oil (both from Sigma-Aldrich, Saint Louis, Mo., U.S.A.) in a 30 ml vial. The vial was the placed in a 70° C. water bath for 60 min, and a clear low viscosity solution was obtained. The combination was then emulsified into the gelatin solution with a four-blade mixer. An oil-in-water emulsion was formed with a median size of 8 μm analyzed with AccuSizer™ 780, (Particle Sizing Systems, Santa Barbara, Calif., U.S.A.). After 312 grams of deionized water was added to the reactor, the mixture was cooled to 40° C., and the previously prepared sodium polyphosphate solution was added into the reactor. The pH was adjusted to 4.8 with 10% phosphoric acid solution. During pH adjustment and the cooling steps following the pH adjustment, a coacervate, formed from gelatin and polyphosphate, coated onto the oil droplets to form microcapsules. The capsule shells were cross linked with 8 grams of Activa TI (Ajinomoto U.S.A.) containing transglutaminase. The microcapsules suspended in water were then spray dried to obtain a free-flowing powder.

Example 5B

Preparation of Microcapsules Containing 50% Candelilla Wax and 50% Cedarwood Oil The microcapsules were prepared in accordance with the method of Example 5A except that the capsule core contained a combination of 7.5 grams of candelilla wax and 7.5 grams of cedarwood oil.

Example 5C

Preparation of Microcapsules Containing 70% Candelilla Wax and 30% Cedarwood Oil The microcapsules were prepared in accordance with the method of Example 5A except that the capsule core contained a combination of 10.5 grams of candelilla wax and 4.5 grams of cedarwood oil.

Example C6

Preparation of Microcapsules Containing Orange Oil

The microcapsules were prepared in accordance with the method of Example C5 except that the capsule core contained orange oil.

Example 6A

Preparation of Microcapsules Containing 30% Candelilla Wax and 70% Orange Oil

The microcapsules were prepared in accordance with the method of Example 5A except that the capsule core contained a combination of 4.5 grams of candelilla wax and 10.5 grams of orange oil.

Example 6B

Preparation of Microcapsules Containing 50% Candelilla Wax and 50% Orange Oil

The microcapsules were prepared in accordance with the method of Example 5B except that the capsule core contained a combination of 7.5 grams of candelilla wax and 7.5 grams of orange oil.

Example 6C

Preparation of Microcapsules Containing 70% Candelilla Wax and 30% Orange Oil

The microcapsules were prepared in accordance with the method of Example 5C except that the capsule core contained a combination of 10.5 grams of candelilla wax and 4.5 grams of orange oil.

Example C7

Preparation of Microcapsules Containing Lemon Oil

The microcapsules were prepared in accordance with the method of Example C5 except that the capsule core contained lemon oil.

Example 7A

Preparation of Microcapsules Containing 30% Candelilla Wax and 70% Lemon Oil

The microcapsules were prepared in accordance with the method of Example 5A except that the capsule core contained a combination of 4.5 grams of candelilla wax and 10.5 grams of lemon oil.

Example 7B

Preparation of Microcapsules Containing 50% Candelilla Wax and 50% Lemon Oil

The microcapsules were prepared in accordance with the method of Example 5B except that the capsule core contained a combination of 7.5 grams of candelilla wax and 7.5 grams of lemon oil.

Example 7C

Preparation of Microcapsules Containing 70% Candelilla Wax and 30% Lemon Oil

The microcapsules were prepared in accordance with the method of Example 5C except that the capsule core contained a combination of 10.5 grams of candelilla wax and 4.5 grams of lemon oil.

TABLE 2

Examples of Prepared Microcapsules with Candelilla Wax

| Example | Oil | Percentage Candelilla Wax |
|---|---|---|
| C5 | Cedarwood | 0 |
| 5A | Cedarwood | 30 |
| 5B | Cedarwood | 50 |

TABLE 2-continued

Examples of Prepared Microcapsules with Candelilla Wax

| Example | Oil | Percentage Candelilla Wax |
|---|---|---|
| 5C | Cedarwood | 70 |
| C6 | Orange | 0 |
| 6A | Orange | 30 |
| 6B | Orange | 50 |
| 6C | Orange | 70 |
| C7 | Lemon | 0 |
| 7A | Lemon | 30 |
| 7B | Lemon | 50 |
| 7C | Lemon | 70 |

Examples 8-10

In separate runs, microcapsules were prepared according to the procedure heretofore described, the microcapsules containing in the core an essential oil or a flavor oil, and a paraffin wax (BW-407). The microcapsules contained a flavor oil selected from cedarwood oil, orange oil, or lemon oil. For each oil, three sets of microcapsules were prepared; the microcapsules containing 0% paraffin wax, 50% paraffin wax and 70% paraffin wax, respectively. These examples are enumerated in Table 3.

Example C8

Preparation of Microcapsules Containing Cedarwood Oil (No Paraffin Wax)

The microcapsules were prepared in accordance with the method of Example C5.

Example 8A

Preparation of Microcapsules Containing 50% Paraffin Wax and 50% Cedarwood Oil 31.8 grams of gelatin (Sigma-Aldrich, Saint Louis, Mo., U.S.A.) was mixed with 423 grams of deionized water in a jacketed reactor at 70° C. until completely dissolved. A sodium polyphosphate solution was prepared by dissolving 3.2 grams of sodium polyphosphate in 61 grams of deionized water. A combination of BW407 wax and cedarwood oil was obtained by mixing 7.5 grams of BW407 wax (from Blended Wax, Inc., Oshkosh, Wis.) with 7.5 grams of cedarwood oil (from Sigma-Aldrich, Saint Louis, Mo., U.S.A.) in a 30 ml vial. The vial was the placed in a 70° C. water bath for 60 min, and a clear low viscosity solution was obtained. The combination was then emulsified into the gelatin solution with a four-blade mixer. An oil-in-water emulsion was formed with a median size of 8 µm analyzed with AccuSizer™ 780, (Particle Sizing Systems, Santa Barbara, Calif., U.S.A.). After 312 grams of deionized water was added to the reactor, the mixture was cooled to 40° C., and the previously prepared sodium polyphosphate solution was added into the reactor. The pH was adjusted to 4.8 with 10% phosphoric acid solution. During pH adjustment and the cooling steps following the pH adjustment, a coacervate, formed from gelatin and polyphosphate, coated onto the oil droplets to form microcapsules. The capsule shells were cross linked with 8 grams of Activa TI (Ajinomoto U.S.A.) containing transglutaminase. The microcapsules suspended in water were then spray dried to obtain a free-flowing powder.

Example 8B

Preparation of Microcapsules Containing 70% Paraffin Wax and 30% Cedarwood Oil

The microcapsules were prepared in accordance with the method of Example 8A except that the capsule core contained a combination of 10.5 grams of paraffin wax and 4.5 grams of cedarwood oil.

Example C9

Preparation of Microcapsules Containing Orange Oil (No Paraffin Wax)

The microcapsules were prepared in accordance with the method of Example C6.

Example 9A

Preparation of Microcapsules Containing 50% Paraffin Wax and 50% Orange Oil

The microcapsules were prepared in accordance with the method of Example 8A except that the capsule core contained a combination of 7.5 grams of paraffin wax and 7.5 grams of orange oil.

Example 9B

Preparation of Microcapsules Containing 70% Paraffin Wax and 30% Orange Oil

The microcapsules were prepared in accordance with the method of Example 8B except that the capsule core contained a combination of 10.5 grams of paraffin wax and 4.5 grams of orange oil.

Example C10

Preparation of Microcapsules Containing Lemon Oil

The microcapsules were prepared in accordance with the method of Example C7.

Example 10A

Preparation of Microcapsules Containing 50% Paraffin Wax and 50% Lemon Oil

The microcapsules were prepared in accordance with the method of Example 8A except that the capsule core contained a combination of 7.5 grams of paraffin wax and 7.5 grams of lemon oil.

Example 10B

Preparation of Microcapsules Containing 70% Paraffin Wax and 30% Lemon Oil

The microcapsules were prepared in accordance with the method of Example 8B except that the capsule core contained a combination of 10.5 grams of paraffin wax and 4.5 grams of lemon oil.

From a composition standpoint, Example 9A is similar to Example E; Example 9B is similar to Example F; Example 10A is similar to Example G; and Example 10B is similar to Example 3D. The hardness and flowability characteristics of these combinations of carrier material and flavor oils can be ascertained from Table 1. Example E described in Table 1 provides the characteristics of Example 9A; Example F corresponds to Example 9B; Example G corresponds to Example 10A; and Example 3D corresponds to Example 10B.

TABLE 3

Examples of Prepared Microcapsules with BW-407 Paraffin Wax.

| Example | Oil | Percentage BW-407 Wax |
|---|---|---|
| C8 | Cedarwood | 0 |
| 8A | Cedarwood | 50 |
| 8B | Cedarwood | 70 |
| C9 | Orange | 0 |
| 9A | Orange | 50 |
| 9B | Orange | 70 |
| C10 | Lemon | 0 |
| 10A | Lemon | 50 |
| 10B | Lemon | 70 |

To determine release properties of the heretofore prepared microcapsules, in each case 50 grams of the prepared capsule slurry was placed into a 4 oz glass bottle and 50 ml hexane was introduced to the bottle. The starting slurry was a 3% w/w aqueous slurry of microcapsules. The hexane was poured slowly into the microcapsule slurry without agitation. The mixtures were stored at 22° C. in a covered container in a darkened area. After discrete periods of time, as indicated in the ordinate on each of the graphs set forth as FIGS. 1-6 and in the tables below, hexane was recovered. The recovered hexane was analyzed in a spectrophotometer to determine the concentration of the indicated oil.

An Agilent 8453 UV-Visible Spectroscopy System spectrometer was used to determine the wavelength of maximum absorption for the active oil in question. For the oils evaluated, the following wavelengths were determined:

Cedarwood oil—252 nm

Orange oil—310 nm

Lemon oil—305 nm

Additionally, a series of oil solutions in hexane were evaluated in the spectrometer to form a calibration curve.

Hexane was removed from the microcapsule mixture and evaluated in the spectrometer at the indicated wavelength. Using the calibration curve previously determined, the concentration of the active oil in hexane was determined and was expressed as mg/ml.

The following tables, and FIGS. 1-6 respectively, depict the results of this analysis.

TABLE 4

Release of Cedarwood Oils with Candelilla Wax (Examples C5, 5A, 5B, and 5C)

| T (hours) | 0% Wax | 30% Wax | 50% Wax | 70% Wax |
|---|---|---|---|---|
| 0.167 | 0.05 | 0.06 | 0.06 | 0.00 |
| 0.334 | 0.08 | 0.16 | 0.12 | 0.01 |
| 2 | 0.01 | 0.10 | 0.11 | 0.01 |
| 24 | 0.17 | 0.11 | 0.09 | 0.02 |
| 48 | 0.25 | 0.20 | 0.17 | 0.02 |
| 168 | 0.31 | 0.26 | 0.21 | 0.03 |
| 336 | 0.34 | 0.25 | 0.23 | 0.04 |
| 672 | 0.40 | 0.31 | 0.30 | |

TABLE 5

Release of Orange Oils with Candelilla Wax (Examples C6, 6A, 6B, and 6C)

| T (hours) | 0% Wax | 30% Wax | 50% Wax | 70% Wax |
|---|---|---|---|---|
| 0.167 | 0.06 | 0.04 | 0.03 | 0.04 |
| 1 | 0.11 | 0.11 | 0.11 | 0.07 |
| 2 | 0.15 | 0.12 | 0.12 | 0.09 |
| 24 | 0.65 | 0.51 | 0.45 | 0.32 |
| 48 | 1.09 | 0.85 | 0.69 | 0.40 |
| 168 | 1.66 | 1.37 | 1.14 | 0.58 |
| 336 | 2.24 | 1.98 | 1.75 | 0.70 |
| 672 | 2.64 | 2.22 | 1.72 | |

TABLE 6

Release of Lemon Oils with Candelilla Wax (Examples C7, 7A, 7B, and 7C)

| T (hours) | 0% Wax | 30% Wax | 50% Wax | 70% Wax |
|---|---|---|---|---|
| 0.167 | 0.10 | 0.07 | 0.06 | 0.03 |
| 1 | 0.18 | 0.13 | 0.10 | 0.06 |
| 2 | 0.25 | 0.20 | 0.16 | 0.07 |
| 24 | 0.67 | 0.53 | 0.43 | 0.36 |
| 48 | 1.00 | 0.77 | 0.61 | 0.46 |
| 168 | 1.63 | 1.18 | 0.98 | 0.63 |
| 336 | 1.93 | 1.31 | 1.02 | 0.63 |
| 672 | 2.15 | 1.37 | 1.12 | |

TABLE 7

Release of Cedarwood Oils with BW407 Wax (Examples C8, 8A, and 8B)

| T (hours) | 0% BW407 | 50% BW407 | 70% BW407 |
|---|---|---|---|
| 0.167 | 0.00 | 0.00 | 0.00 |
| 1 | 0.00 | 0.00 | 0.00 |
| 2 | 0.00 | 0.10 | 0.05 |
| 24 | 0.15 | 0.11 | 0.08 |
| 48 | 0.21 | 0.16 | 0.15 |
| 168 | 0.34 | 0.21 | 0.20 |
| 336 | 0.36 | 0.23 | 0.22 |
| 672 | 0.44 | 0.28 | 0.25 |

TABLE 8

Release of Orange Oils with BW407 Wax (Examples C9, 9A, and 9B)

| T (hours) | 0% BW407 | 50% BW407 | 70% BW407 |
|---|---|---|---|
| 0.167 | 0.10 | 0.09 | 0.06 |
| 1 | 0.27 | 0.27 | 0.21 |
| 2 | 0.22 | 0.19 | 0.11 |
| 24 | 0.75 | 0.60 | 0.52 |
| 48 | 1.15 | 0.80 | 0.70 |
| 168 | 2.13 | 1.29 | 1.11 |
| 336 | 2.19 | 1.68 | 1.33 |
| 672 | 3.00 | 2.72 | 1.65 |

TABLE 9

Release of Lemon Oils with BW407 Wax
(Examples C10, 10A, and 10B)

| T (hours) | 0% BW407 | 50% BW407 | 70% BW407 |
| --- | --- | --- | --- |
| 0.167 | 0.08 | 0.06 | 0.05 |
| 1 | 0.11 | 0.07 | 0.05 |
| 2 | 0.15 | 0.11 | 0.13 |
| 24 | 0.63 | 0.27 | 0.16 |
| 48 | 0.94 | 0.34 | 0.28 |
| 168 | 1.46 | 0.55 | 0.46 |
| 336 | 1.63 | 0.63 | 0.44 |
| 672 | 1.76 | 0.84 | 0.60 |

As indicated therein, the concentration of the exemplary volatile materials did not exceed 2 mg per ml in hexane even after 168 hours. For cedarwood oil, the concentration remained below 0.35 mg/ml even after 338 hours. This data is believed to correlate to an excellent taste masking property. In each case, the concentration was less than the carrier-free hexane concentration.

The foregoing analytical methodology may be generalized to other active materials.

Example 11

Microcapsules prepared in accordance with Example 6A are added to a beverage product in an amount of 5% by weight.

Example 12

A medicinal product is prepared by adding an alkaloid medicinal ingredient to candelilla wax (candelilla wax heated to oil or liquefied state) in the ratio of 30% alkaloid/70% candelilla wax. Microcapsules are prepared according to the heretofore described techniques, and are employed in a children's' oral medicine.

It is thus seen that microcapsules may be prepared in accordance with the foregoing teachings.

Uses of singular terms such as "a," "an," are intended to cover both the singular and the plural, unless otherwise indicated herein or clearly contradicted by context. The terms "comprising," "having," "including," and "containing" are to be construed as open-ended terms. All references, including publications, patent applications, and patents, cited herein are hereby incorporated by reference. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. An encapsulated product comprising:
a plurality of single wall microcapsules, each comprising a wall material, a payload material and carrier material, the payload material and carrier material forming a combination that is at least substantially solid at room temperature but that is sufficiently flowable at a milling temperature of 40-75° C. to permit milling and subsequent encapsulation within said wall material, said carrier material comprising a wax, said combination being disposed within the microcapsule single wall, said combination comprising a solution at said milling temperature, wherein said wall material is gelatin, said microcapsules exhibiting a 168-hour hexane extraction concentration of less than 2 mg/ml.

2. An encapsulated product according to claim 1, said carrier material being selected from the group consisting of candelilla wax and paraffin wax.

3. An encapsulated product according to claim 1, said payload material comprising an oil or an oil-soluble or -dispersible bioactive, pharmaceutical, or nutraceutical.

4. An encapsulated product according to claim 1, said payload material comprising an oil selected from a volatile oil, a flavor oil, or an essential oil.

5. An encapsulated product according to claim 1, said combination having a viscosity of 1200 centipoise or less at 75° C.

6. An encapsulated product according to claim 1, said microcapsules exhibiting a 168-hour hexane extraction concentration of less than 1 mg/ml.

7. An encapsulated product according to claim 1, said microcapsules exhibiting a 168-hour hexane extraction concentration of less than 0.5 mg/ml.

8. A comestible product comprising encapsulated material according to claim 1 and an additional flavoring material.

9. An encapsulated product according to claim 2, said payload material comprising an oil or an oil-soluble or -dispersible bioactive, pharmaceutical, or nutraceutical.

10. An encapsulated product according to claim 2, said payload material comprising an oil selected from a volatile oil, a flavor oil, or an essential oil.

11. An encapsulated product according to claim 2, said combination having a viscosity of 1200 centipoise or less at 75° C.

12. An encapsulated product according to claim 2, said of microcapsules exhibiting a 168-hour hexane extraction concentration of less than 1 mg/ml.

13. An encapsulated product according to claim 2, said microcapsules exhibiting a 168-hour hexane extraction concentration of less than 0.5 mg/ml.

\* \* \* \* \*